(12) United States Patent
Gerber et al.

(10) Patent No.: US 7,976,534 B2
(45) Date of Patent: Jul. 12, 2011

(54) EVENT TRIGGERED INFECTION MONITORING

(75) Inventors: Martin T. Gerber, Maple Grove, MN (US); John C. Rondoni, Plymouth, MN (US)

(73) Assignee: Medtronic, Inc., Minneapolis, MN (US)

( * ) Notice: Subject to any disclaimer, the term of this patent is extended or adjusted under 35 U.S.C. 154(b) by 0 days.

(21) Appl. No.: 12/510,595

(22) Filed: Jul. 28, 2009

(65) Prior Publication Data

US 2009/0299153 A1 Dec. 3, 2009

Related U.S. Application Data

(62) Division of application No. 11/737,160, filed on Apr. 19, 2007, now abandoned.

(51) Int. Cl.
*A61K 9/22* (2006.01)

(52) U.S. Cl. ... 604/891.1; 604/65; 604/502; 604/288.01

(58) Field of Classification Search ............... 600/549; 604/890.1, 65–67, 131, 891.1, 502, 288.01
See application file for complete search history.

(56) References Cited

U.S. PATENT DOCUMENTS

| | | | |
|---|---|---|---|
| 4,082,097 A | 4/1978 | Mann | |
| 5,029,582 A | 7/1991 | Lekholm | |
| 5,181,905 A | 1/1993 | Flam | |
| 5,546,955 A | 8/1996 | Wilk | |
| 5,807,270 A | 9/1998 | Williams | |
| 5,820,263 A | 10/1998 | Ciobanu | |
| 6,016,447 A | 1/2000 | Juran | |
| 6,113,539 A | 9/2000 | Ridenour | |
| 6,248,080 B1 * | 6/2001 | Miesel et al. | 600/561 |
| 6,282,444 B1 | 8/2001 | Kroll | |
| 6,356,774 B1 | 3/2002 | Bernstein | |
| 6,558,351 B1 | 5/2003 | Steil | |
| 6,901,296 B1 | 5/2005 | Whitehurst | |
| 6,963,772 B2 | 11/2005 | Bloom | |
| 6,970,741 B1 | 11/2005 | Whitehurst | |
| 7,049,824 B2 | 5/2006 | Shabino | |
| 7,171,252 B1 | 1/2007 | Scarantino | |
| 2002/0042596 A1 | 4/2002 | Hartlaub | |
| 2003/0032892 A1 | 2/2003 | Ertach | |
| 2003/0194752 A1 | 10/2003 | Anderson | |

(Continued)

FOREIGN PATENT DOCUMENTS

DE 10150343 4/2003

OTHER PUBLICATIONS

U.S. Appl. No. 60/825,101, filed Sep. 2006, Lee.

(Continued)

*Primary Examiner* — Kevin C Sirmons
*Assistant Examiner* — Deanna K Hall
(74) *Attorney, Agent, or Firm* — Campbell Nelson Whipps LLC

(57) ABSTRACT

Implantable medical devices include a sensor module capable of detecting an indicator of infection in proximity to the device. The sensor module is activated following a detection of an event associated with the device, such as, for example, refill of an implantable infusion device or implantation. The sensor module is deactivated two or more hours following activation. Methods include detecting a first event associated with an implanted medical device; activating a sensor module of the implanted medical device at or after the detection of the first event; deactivating the sensor module two hours or more after the sensor module is activated; and determining whether information regarding the indicator of infection is indicative of an infection.

19 Claims, 12 Drawing Sheets

U.S. PATENT DOCUMENTS

| | | |
|---|---|---|
| 2003/0199783 A1 | 10/2003 | Bloom |
| 2003/0216677 A1 | 11/2003 | Pan |
| 2004/0066313 A1 | 4/2004 | Ong |
| 2004/0236192 A1 | 11/2004 | Necola Shehada |
| 2005/0012610 A1 | 1/2005 | Liao |
| 2005/0090761 A1 | 4/2005 | Carney |
| 2005/0096584 A1 | 5/2005 | Ferek-Petric |
| 2005/0171580 A1 | 8/2005 | MacDonald |
| 2006/0047218 A1 | 3/2006 | Bloom |
| 2006/0062852 A1 | 3/2006 | Holmes |
| 2006/0079793 A1 | 4/2006 | Mann |
| 2006/0149331 A1 | 7/2006 | Mann |
| 2006/0224088 A1 | 10/2006 | Roche |
| 2006/0271108 A1 | 11/2006 | Libbus |
| 2008/0064980 A1 | 3/2008 | Lee |
| 2008/0262323 A1 | 10/2008 | Gerber |
| 2008/0262331 A1 | 10/2008 | Gerber |
| 2008/0262332 A1 | 10/2008 | Gerber |
| 2008/0262378 A1 | 10/2008 | Gerber |
| 2008/0262379 A1 | 10/2008 | Gerber |
| 2009/0005770 A1 | 1/2009 | Gerber |

OTHER PUBLICATIONS

PCT International Search Report dated Dec. 5, 2007.

* cited by examiner

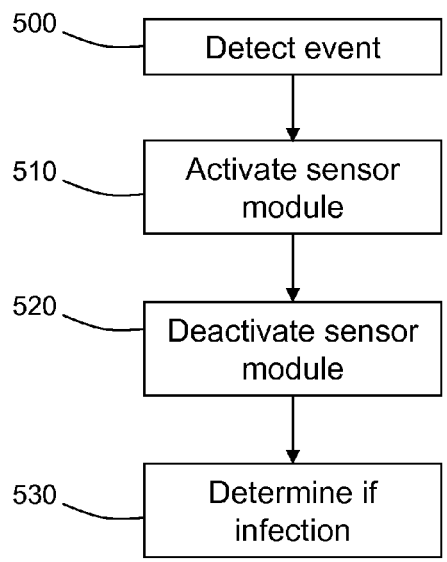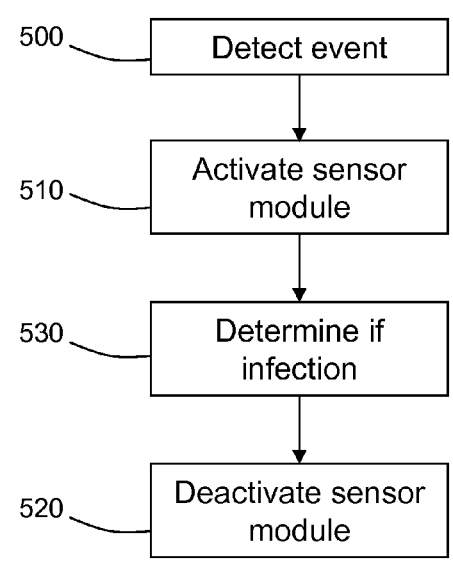
FIG. 9A
FIG. 9B

EVENT TRIGGERED INFECTION MONITORING

RELATED APPLICATION

This is a divisional application of U.S. patent application Ser. No. 11/737,160 filed Apr. 19, 2007, now abandoned.

FIELD

This disclosure relates, inter alia, to implantable medical devices. More particularly, it relates to systems, devices and methods for monitoring infection in proximity to medical devices implanted in patients.

BACKGROUND

Infection associated with implantation of medical devices is a serious health and economic concern. Today, infections associated with implanted medical devices are not very common due to care and precautions taken during surgical implantation of the devices. However, when infection associated with an implanted medical device (IMD) does occur, explanting the device is often the only appropriate course of action.

For IMDs having a battery powered component, such as implantable cardiac pacemakers, cardioverter/defibrillators having pacing capabilities, other electrical stimulators including spinal cord, deep brain, nerve, and muscle stimulators, infusion devices, cardiac and other physiologic monitors, cochlear implants, etc., the battery powered component is typically enclosed in a housing that is implanted subcutaneously at a surgically prepared site, referred to as a "pocket". Associated devices, such as elongated medical electrical leads or drug delivery catheters, extend from the pocket to other subcutaneous sites or deeper into the body to organs or other implantation sites.

Surgical preparation and implantation are conducted in a sterile field, and the IMD components are packaged in sterile containers or sterilized prior to introduction into the sterile field. However, despite these precautions, there always is a risk of introduction of microbes into the pocket. Surgeons therefore typically apply disinfectant or antiseptic agents to the skin at the surgical site prior to surgery, directly to the site before the incision is closed, and prescribe oral antibiotics for the patient to ingest during recovery.

Despite these precautions, infections do occur. In addition, once the pocket becomes infected, the infection can migrate along the lead or catheter to the heart, brain, spinal canal or other location in which the lead or catheter is implanted. Such a migrating infection can become intractable and life-threatening, requiring removal of the IMD in the pocket and associated devices, such as leads and catheters. Removal of a chronically implanted lead or catheter can be difficult and dangerous. Accordingly, aggressive systemic drug treatment is prescribed to treat such infections. However, early detection of infection associated with implanted medical devices may allow for earlier intervention, resulting in fewer device explants.

Monitoring of infection through the use of sensors, such as temperature and pH sensors that can provide information indicative of infection, has been proposed. However, monitoring of infection through sensors connected to an IMD can drain battery power of the IMD, particularly if monitoring is constantly performed, even at time where likelihood of infection is very low to non-existent. Such monitoring would result in reducing the useful life of the IMD or increasing the frequency with which the patient will need to recharge the battery.

SUMMARY

The present disclosure describes, inter alia, systems, devices and methods that can be used to monitor an infection following an event associated with an implanted medical device, where a sensor module capable of detecting an indicator of infection is activated following the event and deactivated thereafter. Such devices, systems and methods may be used to detect infection associated with implantable medical devices in a power effective manner.

In an embodiment, a method for monitoring infection in proximity to an implanted medical device is described. The method includes detecting a first event associated with an implanted medical device, such as a risk of infection in proximity to an implanted medical device, and activating a sensor module of the implanted medical device at or after the detection of the first event. The sensor module is capable of obtaining and transmitting information regarding an indicator of infection. The method further includes deactivating the sensor module two hours or more after the sensor module is activated, and determining whether the information regarding the indicator of infection is indicative of an infection. The method may further include issuing an alert to indicate that an infection has been detected in proximity to the implanted device. In some embodiments, the method is carried out entirely within an implanted medical device. In others, the method is carried out in part by an implanted medical device and in part by an external device in wireless communication with the implanted device.

By providing devices, systems and methods that allow for monitoring of infection only during the times when an infection is likely to be present, infections in proximity to an implanted medical device may be monitored in a power efficient manner. In addition, monitoring a given sensed parameter or set of parameters over a period of time allows for data regarding the parameters to be trended to increase the accuracy of the determination as to whether an infection has occurred in proximity to an implanted device. These and other advantages will be readily understood from the following detailed descriptions when read in conjunction with the accompanying drawings.

BRIEF DESCRIPTION OF THE DRAWINGS

FIGS. 9-13 are flow diagrams of representative methods.

Figure 1:
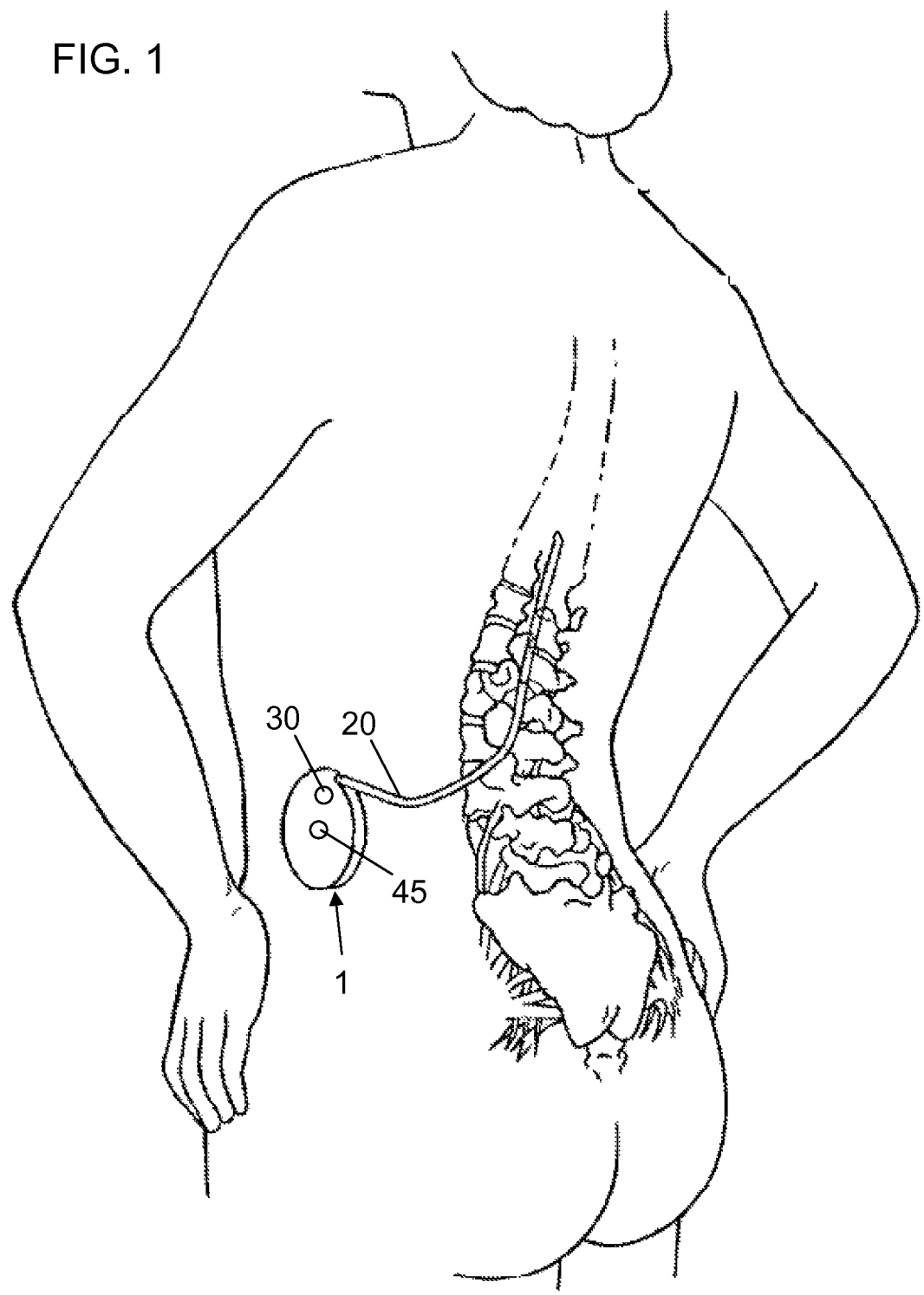
FIG. 1 is a diagrammatic representation of a perspective view of an environment of an implantable infusion system implanted in a patient.

The drawings are not necessarily to scale. Like numbers used in the figures refer to like components, steps and the like. However, it will be understood that the use of a number to refer to a component in a given figure is not intended to limit the component in another figure labeled with the same number.

DETAILED DESCRIPTION

In the following detailed description, reference is made to the accompanying drawings that form a part hereof, and in which are shown by way of illustration several specific embodiments of devices, systems and methods. It is to be understood that other embodiments are contemplated and may be made without departing from the scope or spirit of the present invention. The following detailed description, therefore, is not to be taken in a limiting sense.

All scientific and technical terms used herein have meanings commonly used in the art unless otherwise specified. The definitions provided herein are to facilitate understanding of certain terms used frequently herein and are not meant to limit the scope of the present disclosure.

As used in this specification and the appended claims, the singular forms "a", "an", and "the" encompass embodiments having plural referents, unless the content clearly dictates otherwise. As used in this specification and the appended claims, the term "or" is generally employed in its sense including "and/or" unless the content clearly dictates otherwise.

As used herein, "active implantable medical device" means an implantable medical device that includes a power source to deliver therapy to a patient. Non-limiting examples of active implantable medical devices include implantable infusion devices and implantable electrical signal generators, such as cardiac defibrillators, pacemakers, neurostimulators, gastric stimulators, and cochlear implants. Active implantable medical devices typically are used in conjunction with associated implantable medical devices, such as catheters or leads.

Unless otherwise indicated, all numbers expressing feature sizes, amounts, and physical properties used in the specification and claims are to be understood as being modified in all instances by the term "about." Accordingly, unless indicated to the contrary, the numerical parameters set forth in the foregoing specification and attached claims are approximations that can vary depending upon the desired properties sought to be obtained by those skilled in the art utilizing the teachings disclosed herein.

The recitation of numerical ranges by endpoints includes all numbers subsumed within that range (e.g. 1 to 5 includes 1, 1.5, 2, 2.75, 3, 3.80, 4, and 5) and any range within that range.

The present disclosure describes, inter alia, systems, devices and methods that may be used to monitor infection in proximity to an implanted medical device. The systems, devices and methods monitor infection following an event associated an implantable medical device, such as a risk of infection in proximity to the implanted medical device; e.g., a refill procedure of an implanted infusion device or device implantation. As infection is typically observed within certain time periods following events associated with the device, power may be conserved by activating an infection detecting sensor module during such time periods and deactivating thereafter. For example, it may take several hours following an event such as implantation for an infection to develop to a point capable of being adequately detected, and the likelihood of an infection in proximity to the device drops dramatically after the surgical would has healed. Accordingly, for example, power may be conserved (and thus the longevity of an active implantable device may be increased or the frequency for the need to recharge may be decreased) by activating an infection detecting sensor module on or after device implantation and deactivating the sensor module 30 days or more after implantation, at which time the surgical wound associated with implantation should be sufficiently healed.

Further, as the time at which an infection may develop or be detectable following an event is uncertain, it is desirable to monitor infection after activation of the sensor module until the likelihood of infection has diminished significantly. Accordingly, the sensor module is deactivated two hours or more following activation of the sensor module. For example, the sensor module may be deactivated between two hours and 90 days following activation, between 12 hours and 30 days following activation, between 1 day and 14 days following activation, etc. In addition, monitoring over a period of time allows for trending of data, which can provide a more accurate determination as to whether an infection may be present in proximity to the implanted device.

The teachings described herein may be employed in conjunction with nearly any implantable medical device, including monitoring devices. However, the greatest benefit may be seen with active implantable medical devices—i.e., those having a power source for providing therapy, which power source may otherwise be drained by the constant monitoring of infection during time periods where infection is not likely to be observed.

Figure 2:
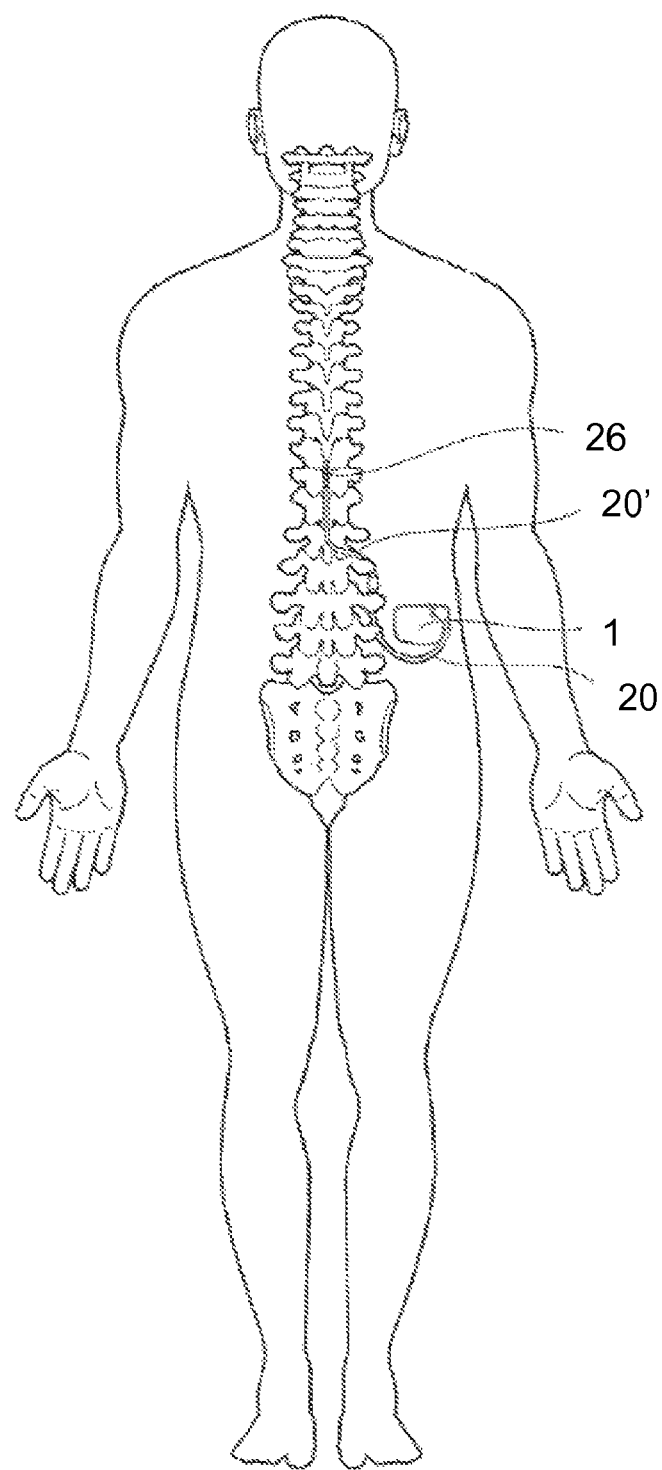
FIG. 2 is a diagrammatic representation of a perspective view of an environment of an implantable electrical signal generator system implanted in a patient
Figure 3A:
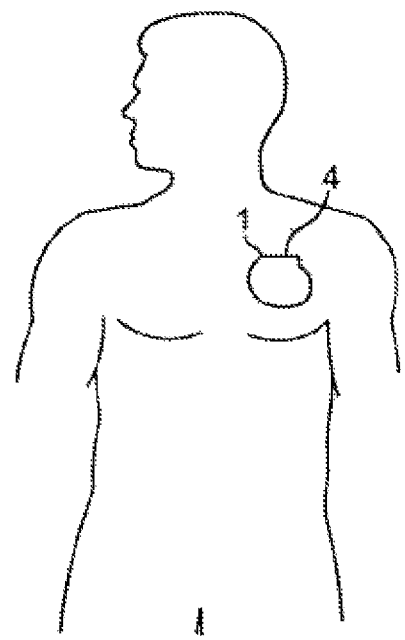
FIGS. 3A-D are a diagrammatic representations of a perspective views of environments of implantable medical devices implanted in patients.
Figure 3B:
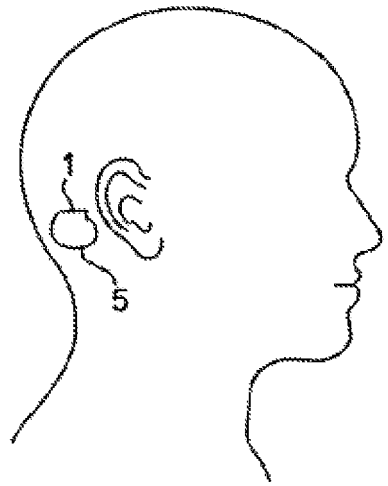
Figure 3C:
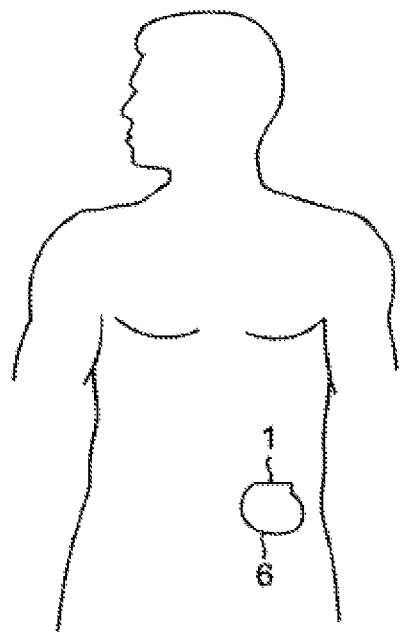
Figure 3D:
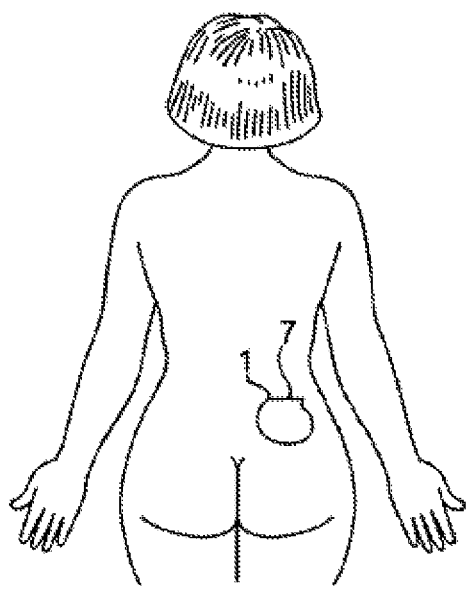

Referring to FIGS. 1 and 2, general representative environments for implanting active medical devices 1 and associated devices 20 are shown. Active medical device 1 is subcutaneously implanted in an abdominal region of a patient. A distal portion of associated device 20 is intrathecally inserted into the patient's spinal canal through a lumbar puncture and advanced rostrally to a desired location (FIG. 1) or epidurally placed along a suitable location of spinal cord (FIG. 2). Proximal end of associated device 20 is tunneled subcutaneously to location of active device 1, where it may be connected to active device 1. While distal portion of associated device 20 is shown in FIGS. 1 and 2 as being located in or on spinal cord, it will be understood that associated device 20 may be placed at any location in patient for which it is desirable to administer therapy generated or delivered by active medical device 1.

In the embodiment shown in FIG. 1, active implantable device 1 is an infusion device, and associated device 20 is a catheter. Catheter 20 is typically a flexible tube with a lumen running from the proximal end of catheter 20 to one or more delivery regions that are typically located at the distal portion of catheter 20. Proximal portion of catheter 20 is connected to infusion device 20. Distal portion of catheter 20 is positioned at a target location in the patient to deliver fluid containing therapeutic agent from infusion device 1 to patient through a delivery region of catheter 20. Infusion device 1, such as Medtronic Inc.'s SynchroMed™ II implantable programmable pump system, includes a reservoir (not shown) for housing a therapeutic substance and a refill port 45 in fluid communication with reservoir. The reservoir may be refilled by percutaneously inserting a needle (not shown) into patient such that needle enters refill port 45, and fluid containing therapeutic substance may be delivered into reservoir from needle via refill port 45. Infusion device 1 shown in FIG. 1 also includes a catheter access port 30 that is in fluid communication with the catheter 20. Fluid may be injected into or withdrawn from patient through catheter 20 via catheter access port 30 by percutaneously inserting a needle into access port 30. Each entry of needle across patient's skin to gain access refill port 45 or access port 30 results in the possibility of infection in proximity to the active medical device 1.

In the embodiment shown in FIG. 2, active implantable device 1 is an electrical signal generator, such as Medtronic Inc.'s Restore™ Advanced implantable neurostimulator, and associated devices 20, 20' are a lead extension 20 and lead 20'. Lead 20' includes one or more electrical contacts (not shown) on its proximal end portion and one or more electrodes on its distal end portion 26. The contacts and electrodes are electrically coupled via wires running through lead 20'. Electrical signals generated by the signal generator 1 may be delivered to lead 20 through the contacts and then to the patient through the electrodes. As shown in FIG. 2, lead 20' may be connected to signal generator 1 through a lead extension 20. Extension 20 includes one or more contacts at the proximal and distal end portions that are electrically coupled through wires running through extension 20. Of course it will be understood that with some systems lead 20' may be directly connected to electrical signal generator 1 without use of a lead extension 20. It will be further understood that more than one lead 20' or lead extension 20 may be employed per signal generator 1.

While FIGS. 1 and 2 depict systems including as active implantable medical devices 1 infusion devices and electrical signal generators, it will be understood that the teachings described herein may be applicable to virtually any known or future developed active implantable medical device and that virtually any non-active implantable medical device may be appropriately adapted and configured to perform according to the teachings provided herein.

Referring to FIG. 3, alternative locations for implanting a medical device 1 are shown. As depicted in FIG. 3A, device 1 may be implanted in the pectoral region 7 of a patient. Alternatively, device 1 may be implanted in the head of a patient, more specifically behind the patient's ear (FIG. 3B), in the patient's abdomen (FIG. 3C) or in the patient's lower back or buttocks (FIG. 3D). Of course, device 1 may be placed in any medically acceptable location in patient.

Figure 4:
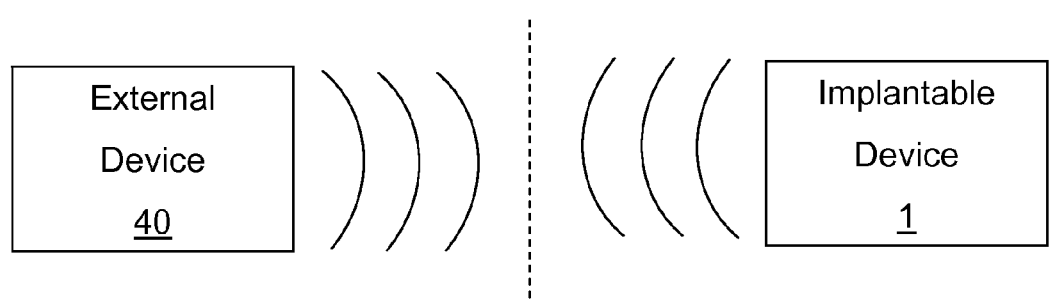
FIG. 4 is a diagrammatic representation of an external device in wireless communication with an implantable medical device.

Referring to FIG. 4, an external device 40 in wireless communication with implantable device 1 is shown. External device 40 may communicate with implantable device 1 through patient's skin, which is represented by the dashed line in FIG. 4. In various embodiments implantable device 1 carries out the various infection monitoring methods, or portions thereof, described herein. In some other embodiments the combination of implantable device 1 and external device 40 carry out the various infection monitoring methods, or portions thereof, described herein. In various embodiments, where implantable device 1 is a programmable device, external device 40 may be a programmer device, such as Medtronic Inc.'s N'Vision™ clinician programmer. Of course external device may be any device capable of wirelessly communicating with implantable device 1, such as a patient programmer, a computer, a personal data assistant, or the like. External device 40 and implantable device 1 may be capable of one-way (external device 40 to implantable device 1 or implantable device 1 to external device 40) or two-way communication.

Figure 5A:
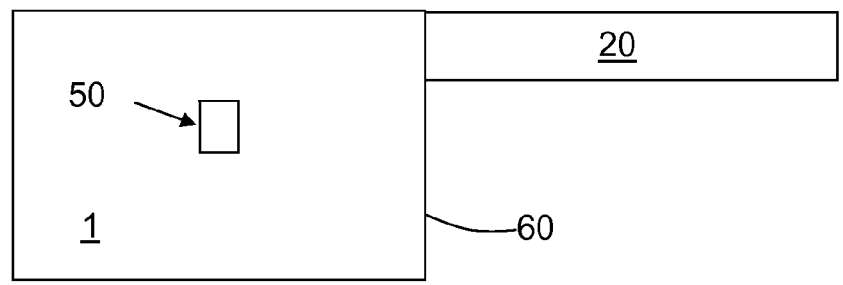
FIGS. 5A-B is a diagrammatic representation of a side view (5A) and back view (B) of an implantable medical device system having sensor(s) in proximity to the implantable device.
Figure 5B:
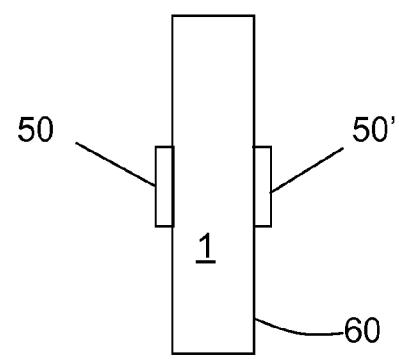

Referring to FIG. 5, sensor(s) 50, 50' associated with implantable active medical device 1 is shown. FIG. 5A is a side view of a representative active device 1 and associated device 20. FIG. 5B is a back view of a representative active device 1. One or more sensor 50, 50' may be located in proximity to device 1; e.g., disposed on, in, or near housing 60 of device 1. Sensor 50, 50' may be any device capable of detecting an obtaining and transmitting information regarding an indicator of infection to device 1. If housing 60 is hermetically sealed, feedthroughs (not shown) may be used to provide electrical connectivity through housing 60 while maintaining the hermetic seal. While not shown, it will be understood that one or more sensor capable of detecting an indicator of infection may be located on, in, or about accessory device 20. Examples of physical or chemical stimuli that may serve as indicators of infection are temperature, impedance, pH, and biological markers of infection.

Changes in temperature in proximity to implanted device 1 may be used as an indicator of infection in proximity to device 1. The temperature of body tissue at a site of infection is generally greater than that of body tissue at a location removed from the site of infection. Accordingly, an increase in temperature in proximity to an implanted medical device 1 may serve as an indicator of infection. Any suitable sensor 50, 50' capable of detecting temperature or changes in temperature may be employed. For example, temperature sensor 50, 50' may include a thermocouple, a thermistor, a junction-based thermal sensor, a thermopile, a fiber optic detector, an acoustic temperature sensor, a quartz or other resonant temperature sensor, a thermo-mechanical temperature sensor, a thin film resistive element, or the like.

Changes in impedance of tissue in proximity to implanted device 1 may be used as an indicator of infection in proximity to device 1. For example, an increase in fluid in tissue is often observed at a site of an infection. Accordingly, a decrease in impedance of tissue in proximity may serve as an indicator of infection. In the case of impedance measurement, detection or monitoring, sensors 50, 50' are electrodes. Impedance may be measured between two electrodes. Current or voltage is applied between the electrode with one electrode at any given time serving as a source and the other serving as a sink. In various embodiments, electrodes will be positioned at opposing surfaces of housing 60 of device 1. In other embodiments, one electrode may be located on accessory device 20, e.g. on a lead, and one may be located on housing of device 1. Alternatively, one electrode may be located on accessory device 20 and housing 60 of device 1 may serve as a return electrode, in a manner similar to unipolar signal generators. Further, it will be understood that more than one electrode pair may be employed to monitor impedance.

In instances where device 1 is an electrical signal generator, the electrical components used for generating therapeutic electrical signals may also be used for generating signals for impedance monitoring. In instances where device 1 is not an electrical signal generator, e.g. device 1 is an infusion pump, components capable of generating appropriate electrical signals for testing impedance of body tissue may be incorporated into device 1. Any impedance detection components or circuitry may be employed. For example, an ohm meter or a wheatstone bridge design may be used to measure or detect changes in impedance or resistance. Examples of additional suitable components or circuitry are described in, for example, the following patents and applications assigned to Medtronic, Inc.: US 2006/0259079; US 2006/0036186; US 2004/0162591; US 2003/0176807; U.S. Pat. No. 5,876,353; U.S. Pat. No. 5,824,029; and U.S. Pat. No. 5,282,840.

Changes in pH in proximity to implanted device 1 may be used as an indicator of infection in proximity to device 1. As pH may serve as a general indicator of the state of a tissue, a change in pH may be indicative of infection. Accordingly, a sudden or gradual change in pH in proximity to an implanted medical device 1 may serve as an indicator of infection. Any suitable sensor 50, 50' capable of detecting pH or changes in pH may be employed.

Any biological markers of infection may be detected in accordance with the teachings presented herein. Non-limiting examples of biological markers of infection include viral, fungal, or bacterial proteins or nucleic acids or fragments thereof. As most infections associated with implantable medical devices appear to be due to infection due to *Staphlococcus aureus*, *Staphlococcus epidermis*, *Pseudomonas aeruginosa* and *Candidia* Sp., detection of proteins, nucleic acids, or fragments thereof of such microorganisms may be beneficial. Alternatively, detection of indicators of an immune response may be detected. For example, an increase in a pro-inflammatory cytokine. Non-limiting examples of proinflammatory cytokines include tumor necrosis factor (TNF; also known as TNFα or cachectin), interleukin (IL)-1α, IL-1β, IL-2; IL-5, IL-6, IL-8, IL-15, IL-18, interferon γ (IFN-γ); platelet-activating factor (PAF), thromboxane; soluble adhesion molecules; vasoactive neuropeptides; phospholipase A2; plasminogen activator inhibitor (PAI-1); free radical generation; neopterin; CD14; prostacyclin; neutrophil elastase; protein kinase; monocyte chemotactic proteins 1 and 2 (MCP-1, MCP-2); macrophage migration inhibitory factor (MIF), high mobility group box protein 1 (HMGB-1), and other known factors. Indication of an immune response may also be detected by an decrease in an anti-inflammatory cytokine in proximity to device 1. Non-limiting examples of anti-inflammatory cytokines include IL-4, IL-10, IL-17, IL-13, IL-1α, and TNFα receptor. It will be recognized that some of proinflammatory cytokines may act as anti-inflammatory cytokines in certain circumstances, and vice-versa. Such cytokines are typically referred to as pleiotropic cytokines. An immune response may also be detected by measuring changes (baseline versus after device implant or other event, a first point after device implant or other event versus a second point after device implant or other event, etc.) in the presence of other factors involved in an immune response. Non-limiting examples of such other factors include TGF, PDGF, VEGF, EGF, FGF, I-CAM, and nitric oxide. In addition, an immune response may be detected by changes in chemokines, such as 6cKine and MIP3beta, and chemokine receptors, including CCR7 receptor. Further, an immune response may be measured by changes in immune cell population (upregulated Langerhans cells, dendritic cells, lymphocytes), or immune cell surface co-stimulatory molecules (Major Histocompatibility, CD80, CD86, CD28, CD40). An immune response may also be detected by measuring changes in other factors involved in the inflammatory cascade, for example in the signal transduction cascades including factors such as NFκ-B, Egr-1, Smads, toll-like receptors, and MAP kinases. In addition, an immune response may be detected by a change in the presence of an exogenous antigen believed to have caused an inflammatory response, such as, e.g., a bacteria, a virus, or a fungus.

Any sensor capable of detecting such biological markers indicative of infection may be used. In various embodiments, a biosensor is used to detect the presence of a molecule in proximity to implanted device 1. Any known or future developed biosensor may be used. The biosensor may have, e.g., an enzyme, an antibody, a receptor, or the like operably coupled to, e.g., a suitable physical transducer capable of converting the biological signal into an electrical signal. In some situations, receptors or enzymes that reversibly bind the molecule being detected may be preferred. In various embodiments, sensor 50, 50' includes an electrode with an ion selective coating that is capable of directly transducing the amount of a particular substance. An example of this type of transducer is described in the paper "Multichannel semiconductor-based electrodes for in vivo electrochemical and electrophysiological studies in rat CNS" by Craig G. van Home, Spencer Bement, Barry J. Hoffer, and Greg A. Gerhardt, published in Neuroscience Letters, 120 (1990) 249-252. In various embodiments, sensor 50, 50' may be a sensor as described in, e.g., U.S. Pat. No. 5,978,702, entitled TECHNIQUES OF TREATING EPILEPSY BY BRAIN STIMULATION AND DRUG INFUSION or U.S. 2005/0209513, entitled COLLECTING SLEEP QUALITY INFORMATION VIA A MEDICAL DEVICE, filed Apr. 15, 2004, and published Sep. 22, 2005. Modifications of the teachings presented in the above-cited references may be made to account for one or more biological marker of infection.

For certain biological markers, e.g. proteins or nucleic acids or fragments thereof of microorganisms responsible for infection, merely the presence of such markers may be indicative of an infection. For other markers that may be present in a patient lacking an infection, e.g. cytokines and chemokines, increases or decreases in the levels of such markers may be indicative of an infection.

For the above-discussed indicators of infection or other indicator of infection, a determination of the presence of infection in proximity to implanted device 1 may be made in any suitable fashion. For example, a determination of infection may be made if a given indicator is detected at, above or below a predetermined threshold value. For example, if a temperature of 101° F. (38.3 C) is detected, a determination may be made that an infection is present in proximity to implanted device 1. Alternatively or in addition, a determination of infection may be made if a given indicator is detected at, above or below a predetermined value for a predetermined period of time. For example, if a temperature of 100° F. (37.8 C) or greater is detected for two hours or more is detected for two hours or more, a determination may be made that an infection is present in proximity to implanted device 1. Of course other types of trends in information regarding indicators of infection may be used advantageously to improve the accuracy of determinations of infections in proximity to an implanted medical device. Additional information regarding use of thresholds determining infection in proximity to an implantable medical device is provided in U.S. patent application Ser. No. 11,737,180, entitled "Indicator Metrics For Infection Monitoring", filed on even date herewith, naming Martin Gerber and John Rondoni as inventors, which application is hereby incorporated herein by reference in its entirety to the extent it does not conflict with the disclosure presented herein.

For the above-discussed indicators of infection or other indicator of infection, it may be desirable to compare levels of the indicators at a location in proximity to device 1 and at a location removed from device. Such comparisons may allow for a reduction in false positive detections. For example, elevation in temperature in proximity to device 1 may be due to localized infection or may be due to increased activity of the patient; increases in inflammatory cytokines in proximity to the device may be due to localized infection or a more general immune response; etc. By comparing the level of an indicator of infection in proximity to an implanted device to the level at a location removed from the device, a more accurate determination of whether an infection is present in proximity to the device may be made. Additional information regarding monitoring an indicator of infection at two locations is provided in U.S. patent application Ser. No. 11/737, 171, entitled "Implantable Therapy Delivery System Having Multiple Temperature Sensors", filed on even date herewith, naming Martin Gerber and John Rondoni as inventors, which application is hereby incorporated herein by reference in its entirety to the extent it does not conflict with the disclosure presented herein.

Information regarding a first indicator of infection may be used to determine whether an infection is present in proximity to the implanted device 1. In addition, one or more second indicators of infection may be used to determine whether the indication based on the first indicator is accurate. Additional information regarding infection monitoring using two or more indicators of infection is provided in U.S. patent application Ser. No. 11/737,181, entitled "Multi-Parameter Infection Monitoring", filed on even date herewith, naming Martin Gerber and John Rondoni as inventors, which application is hereby incorporated herein by reference in its entirety to the extent it does not conflict with the disclosure presented herein.

Figure 6:
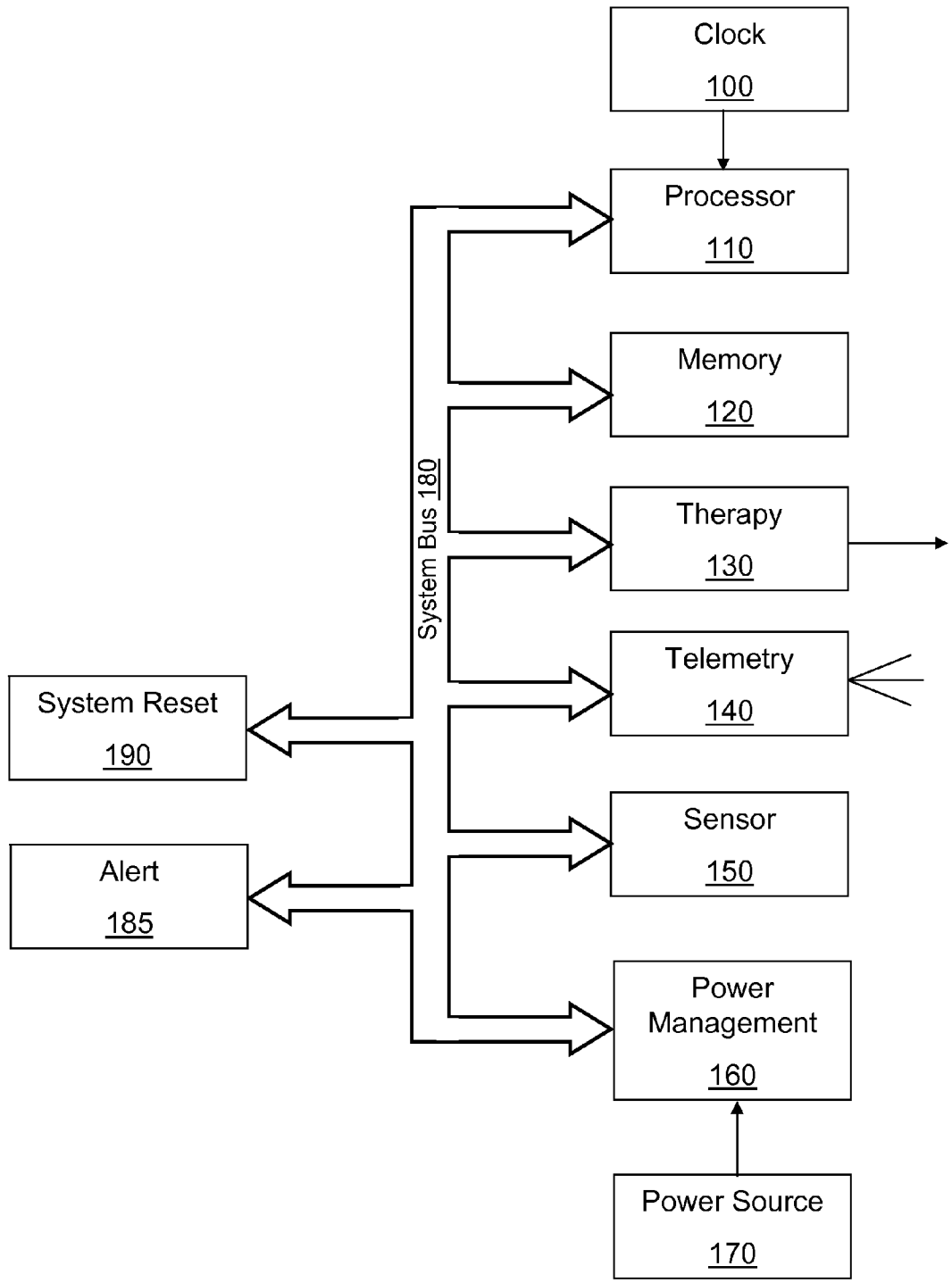
FIG. 6 is a schematic block diagram of representative components of a representative implantable medical device.

Referring to FIG. 6, some representative electronic components of an implantable medical device 1 according to various embodiments are shown in block form. Active implantable medical device 1 as depicted in the embodiment shown in FIG. 6 includes a clock 100, a processor 110, a memory 120, a therapy output or delivery component 130, a telemetry component 140, a sensor 150, a power management module 160, a power source 170, an alert module 185, and a system reset module 190. Other components of active implantable medical device 1 can include, e.g., a diagnostics module (not shown). All components except the power source 170 can be configured on one or more Application Specific Integrated Circuits (ASICs) or may be one or more discrete components, or a combination of both. Also, all components, except the clock and power source are connected to bi-directional data bus 180 that is non-multiplexed with separate address and data lines.

Processor 110 may be synchronous and typically operates on low power, such as Motorola 68HC11 synthesized core operating with a compatible instruction set. Clock 100 counts the number of seconds since a fixed date for date/time stamping of events and may be used for therapy control. Memory 120 includes memory sufficient for operation of device 1, such as volatile Random Access Memory (RAM) for example static RAM, nonvolatile Read Only Memory (ROM), Electrically Erasable Programmable Read Only Memory (EEPROM) for example Flash EEPROM, and register arrays configured on ASICs. Direct Memory Access (DMA) is available to selected modules such as telemetry module 140 or sensor module 150, so that the selected modules can request control of data bus 180 and write data directly to memory 120 bypassing processor 110. System Reset 190 controls operation of ASICs and modules during power-up of device 1, so ASICs and modules registers can be loaded and brought on-line in a stable condition.

Telemetry 140 module or other wireless module provides for communication between implantable device 1 and external device 40 such as a programmer. Communication may be bi-directional. Telemetry module 140 generally includes a telemetry antenna, a receiver, a transmitter, and a telemetry processor. Telemetry modules are generally known in the art and are further detailed in U.S. Pat. No. 5,752,977, entitled "Efficient High Data Rate Telemetry Format For Implanted Medical Device" issued to Grevious et al. (May 19, 1998). While module 140 is referred to herein as "telemetry" module, it will be understood that other forms of wireless communication may readily be substituted where appropriate for telemetry. Examples of forms of wireless communication include Bluetooth®, 802.11, and Medical Implant Communication Service (MICS) frequency band communication.

Therapy module 130 refers to components for carrying out the delivery or generation of therapeutic output to be delivered to a patient from active device 1. One of skill in the art will appreciate that the components may vary on a device-by-device basis and a therapy-by-therapy basis. For example, therapy module 130 may contain an oscillator if device 1 is an electrical signal generator and may contain a pumping mechanism if device 1 is an infusion device.

Sensor module 150 includes a sensor 50, 50', e.g. as discussed with regard to FIG. 5, and may include other components for transmitting sensed information from sensor 50, 50' to, e.g., processor 110 or memory 120. Sensor module 150 or other components of device 1 may include one or more analog to digital converters to convert analog signals generated by sensor 50 into digital signals usable by processor 110, as well as suitable filter and amplifier circuitry.

Alert module 185 may issue an alert, e.g. an audible alert or tactile alert, such as a vibration. An alert may be issued if information indicative of an infection is detected. The alert will serve to prompt the patient to seek medical attention.

It will be understood that the components described in FIGS. 1-6 are but one example of components that an implantable device 1 may have and that many other device or system configurations may be employed to carry out the methods described below. However, for the sake of convenience, the discussion that follows with regard to the methods illustrated in the flow diagrams of FIGS. 7 and 9-13 and device configuration in the block diagram of FIG. 8 will refer to components as described with regard to FIGS. 1-6.

Figure 7:
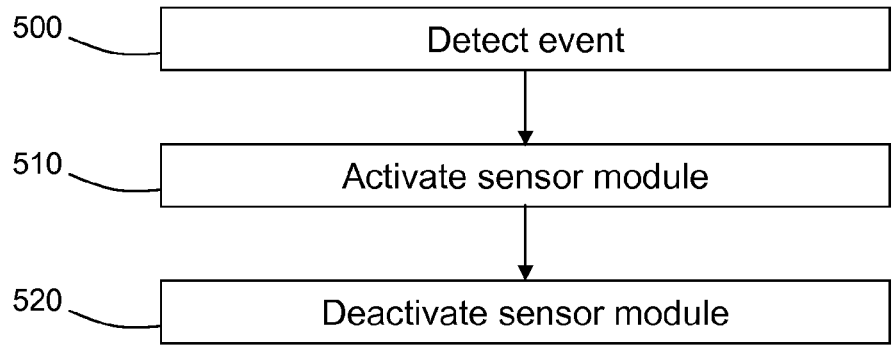
FIG. 7 is a flow diagram of a representative method.

Referring to FIG. 7, a flow diagram of a representative method is shown. According to various embodiments, a method for monitoring an infection in proximity to a medical device includes detecting an event associated with an implanted medical device 1 (500). At or after detection of the event (500), a sensor module 150 of the device 1 is activated (510) and may provide sensed information regarding an indicator of infection to device 1. After activation of the sensor module 150 (510), the sensor module is deactivated (520).

Detection of an event associated with an implanted medical device (500) may include nearly any event that may have an effect on detection of infection or the risk of infection. For example, the event may include implantation or detection of device activation following implantation or a refill or catheter access port procedure of an implanted infusion device. The event may include detection of a recharge event or the end of a recharge event for devices having rechargeable power sources. In some instances (e.g., when monitoring temperature), it may be desirable to wait until several minutes, e.g. ten minutes or more, following a recharge event to activate sensor module (510) (e.g., due to heating caused by recharge process). Additional information regarding events that may adversely affect detection or determination of infection is provided in U.S. patent application Ser. No. 11/737,176, entitled "Refined Infection Monitoring", naming Martin Gerber and John Rondoni as inventors, which application is hereby incorporated herein by reference in its entirety to the extent it does not conflict with the disclosure presented herein. Event detection (500) may include device 1 receiving instructions from an external device, such as a programmer. Alternatively or in addition, event detection (500) may include detection of an event by device 1 or component thereof.

Activation of sensor module (510) may include providing power to a sensor so that the sensor may detect or transmit information regarding an indicator of infection, providing power to allow the sensed information to be stored or processed, or the like. It will be understood that while sensor module 150 is activated, sensed information may be provided continuously to device 1 or may be provided in discrete time intervals; i.e., discontinuously. Discontinuous sensing may serve to provide further power savings to device 1. Deactivation of sensor module (520) in most instances will include undoing the processes undertaken to activate sensor module (510). Activation of sensor module (510) may occur at or following detection of an event (500). In some instances, it may be desirable activate sensor module 150 several minutes or hours after event detection, depending on when after the event an infection is likely to occur. The sensor module 150 may be deactivated (520) at a time when the risk of infection has sufficiently diminished or is nearly nonexistent. In various embodiments, sensor module 150 is deactivated two or more hours following activation. For example, the sensor module may be deactivated between two hours and 90 days following activation, between 12 hours and 30 days following activation, between 1 day and 14 days following activation, etc.

Figure 8:
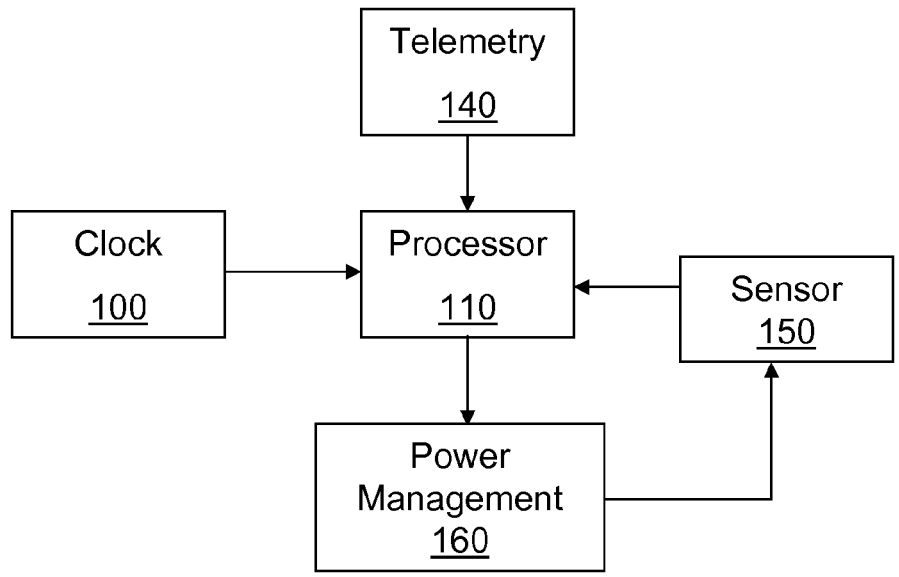
FIG. 8 is a schematic block diagram of representative components of an implantable medical device that may be employed to carryout the method depicted in FIG. 7.

By way of example, FIG. 8 refers to some components of device 1 that may be employed to carry out the method depicted in FIG. 7. For example, detection of an event associated with device 1 (500) may include telemetry module 140 receiving instruction from an external device 40 (See, e.g., FIG. 4), such as a programmer, that device 1 has been implanted. For example, programmer may instruct device 1 via telemetry or other form of wireless communication to initiate system reset module 190. Alternatively, programmer may instruct device 1 via telemetry module 140 that a refill procedure has commenced or completed (if device 1 is an infusion device). Alternatively refill port 30 may comprise a sensor or circuit capable of detecting the presence of a needle, which needle insertion may constitute an event associated with device 1. Regardless of whether an event is detected via internal or external data, processor 110 may be receive such event data, obtain information from clock 100 to time/date stamp the event, instruct power management module 160 to activate sensor module 150. Processor 110 may then instruct power management module 160 to deactivate sensor module 150 once an appropriate length of time has elapsed. As shown in FIG. 8, processor may receive or process information regarding an indication of infection from sensor module 150.

Referring to FIG. 9, the method depicted in FIG. 7 may further include determining whether there is an infection in proximity to device 1 (530). As shown in FIG. 9A, the determination (530) may be made following deactivation of the sensor module (520). Alternatively, as shown in FIG. 9B, the determination (530) may be made prior to deactivation of the sensor module (520). The determination (530) may be made within device, e.g. by processor 110 or detection circuit (not shown), or may be made by external device 40 (see, e.g., FIG. 4). Sensed information may be provided to external device 40 via telemetry module 140.

Figure 10:
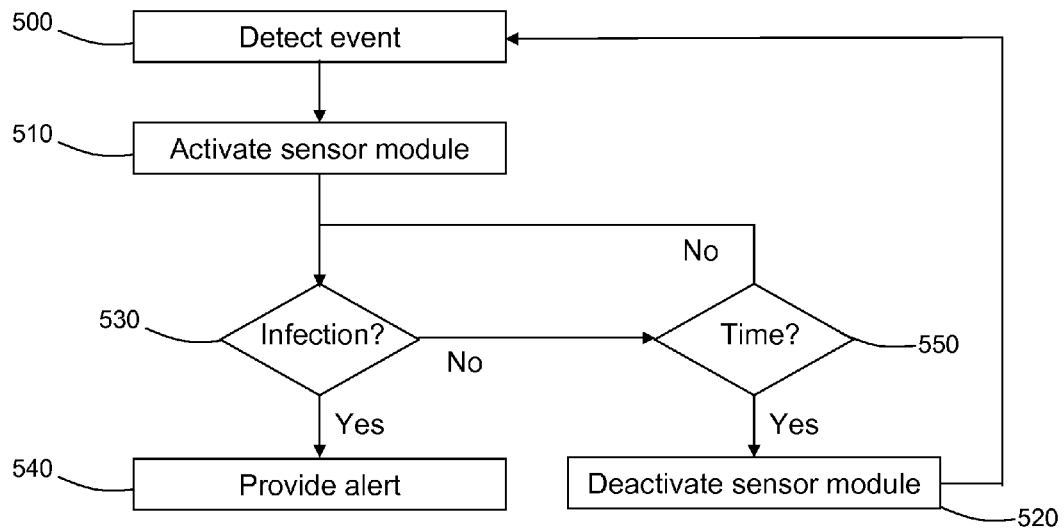

FIGS. 10-13 are flow diagrams illustrating various methods. As shown in FIG. 10, a sensor module capable of detecting information regarding an indicator of infection may be activated (510) during or after detection of an event associated with an implanted medical device (500). A determination may then be made as to whether the information regarding the indicator of infection is indicative of an infection (530). If the sensed information is indicative of an infection, an alert may be provided to the patient (540). The alert may include a sensory indication, such as an audible indication or a tactile indication, such as a vibration, or visual indication. A visual indication may include, for example, text or an image. The alert may be issued by implanted device 1 or an external device 40, such as a programmer. If the indication is visual, the alert will be presented to the patient or clinician by an external device.

If the sensed information is determined to not be indicative of an infection, processor 110 may determine whether a predetermined time limit for sensor activation has expired (550) by obtaining time/date information from clock 100 and comparing to, e.g., time/date stamp associated with event detection (500). If the time limit has passed, processor 110 may instruct power management module 160 to deactivate sensor module 150 (520). If the time limit has not expired, sensor module 150 may continue to provide information regarding an indicator of infection to device 1 and processor 110 may continue to determine whether the sensed information is indicative of infection (530). Once sensor module 150 is deactivated (520), sensor module may be activated (510) on or after detection of a subsequent event (500).

Figure 11:
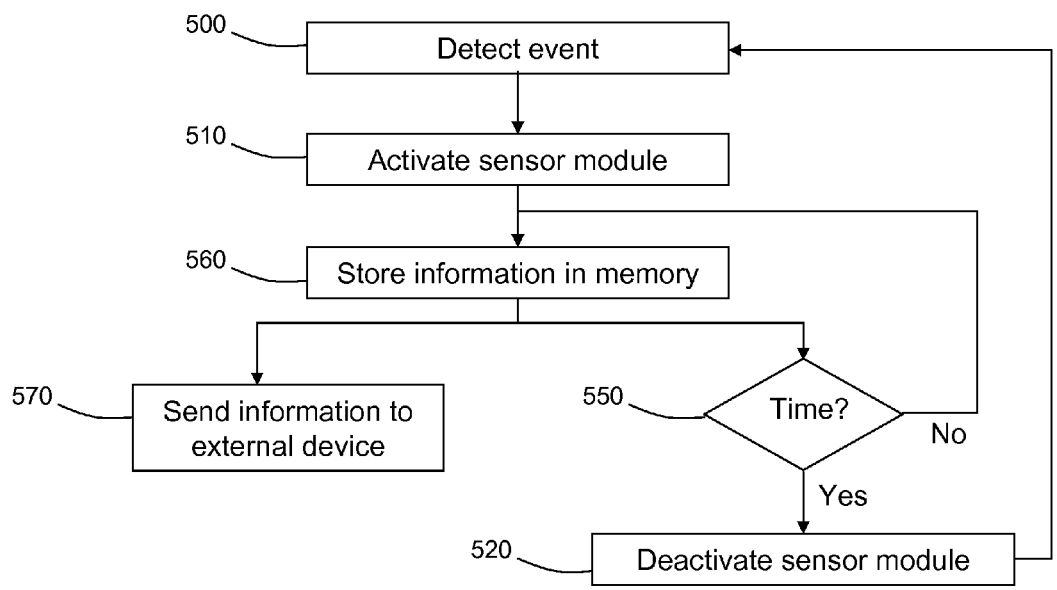

FIG. 11 depicts a flow diagram of a method that may be employed by a system where a determination as to whether the sensed information is indicative of infection is performed by an external device 40 (see, e.g., FIG. 4). As shown in FIG. 11, sensed information is stored in memory 120 (550) while sensor module 150 is active. While sensor module 150 is active or after sensor module 150 has been deactivated (520) sensed information may be sent to external device 40 via telemetry module 140 (570) for a determination of whether the sensed information is indicative of an infection or other analysis.

Figure 12:
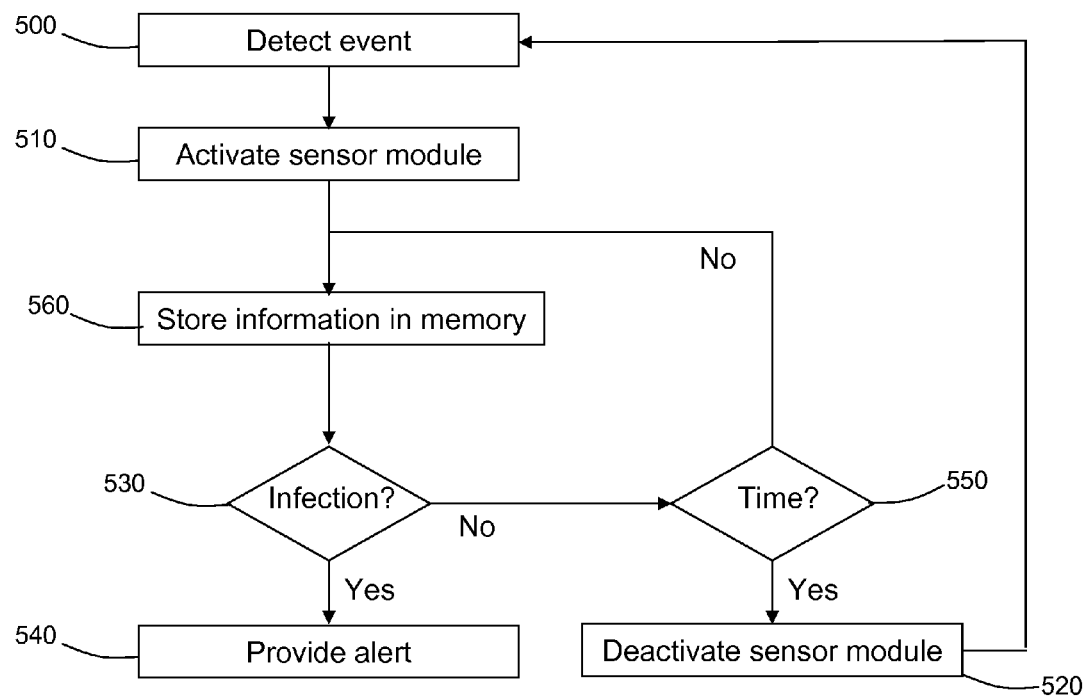
Figure 13:
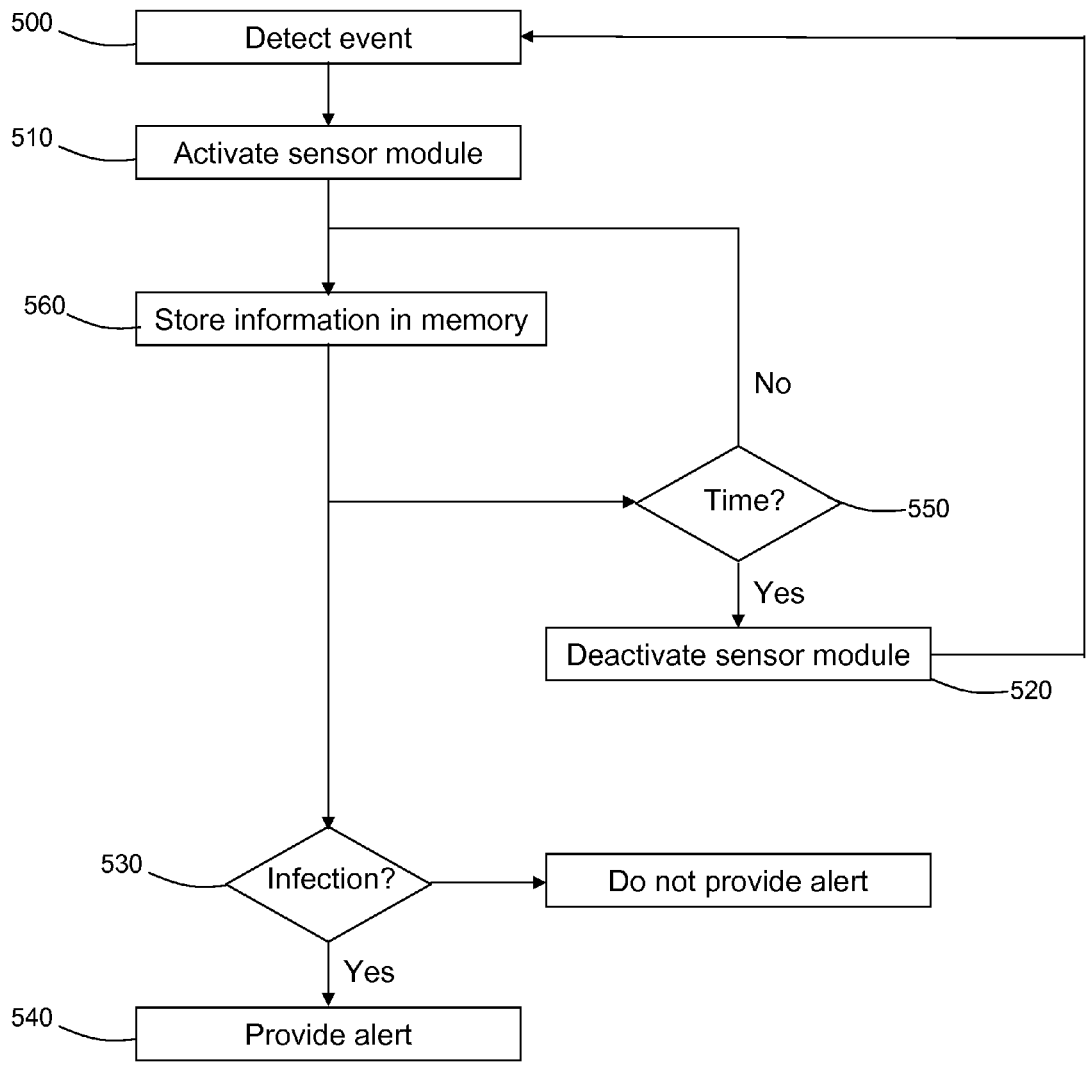

In the embodiments depicted in FIGS. 12 and 13, information may be stored in memory 120 (160) and a determination as to whether the information is indicative of an infection may be made (530) in device 1. In such embodiments, comparisons to prior values can be made and trending of data may occur, e.g. by processor 110 to increase the accuracy of infection detection. As shown in the embodiment depicted in FIG. 12, real-time determination of infection (530) may occur in addition to comparison to prior values and trending. As shown in FIG. 13, the determination (530) may occur in real-time or may occur at predetermined times. Determinations (530) made at pre-determined times rather than continuously or real-time determinations may allow for additional power savings for device 1. An alert may be provided by device 1 (540) if a determination is made that the information is indicative of infection.

Figure 14A:
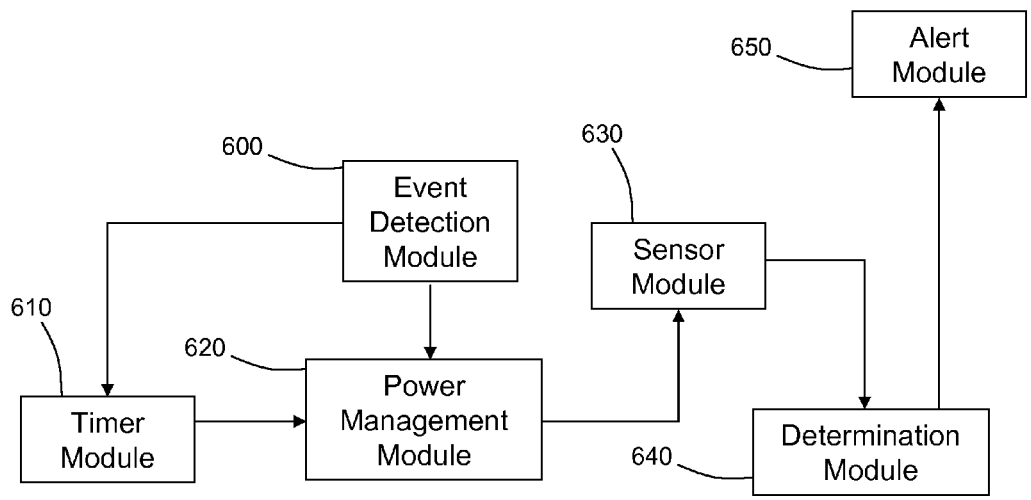
FIGS. 14A-B are schematic block diagrams of a representative implantable medical devices or systems.
Figure 14B:
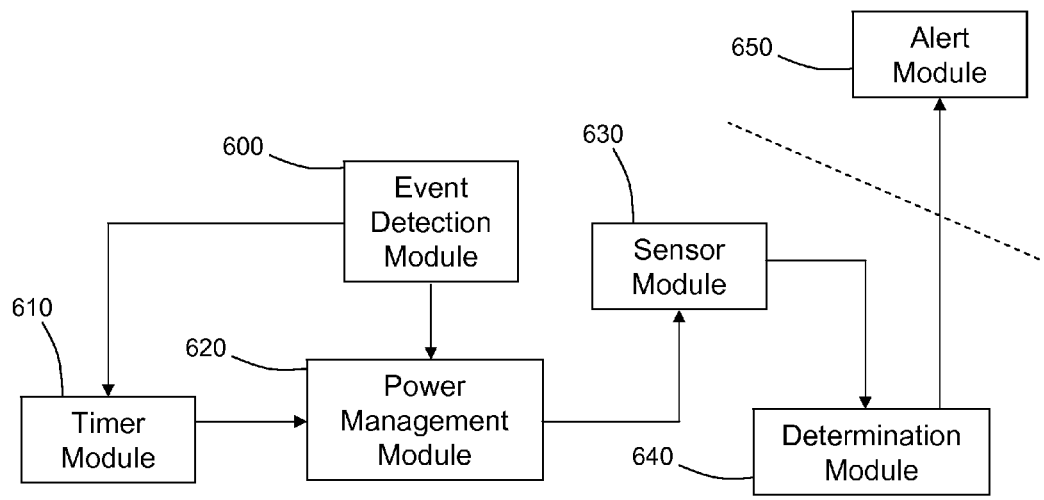
Figure 14C:
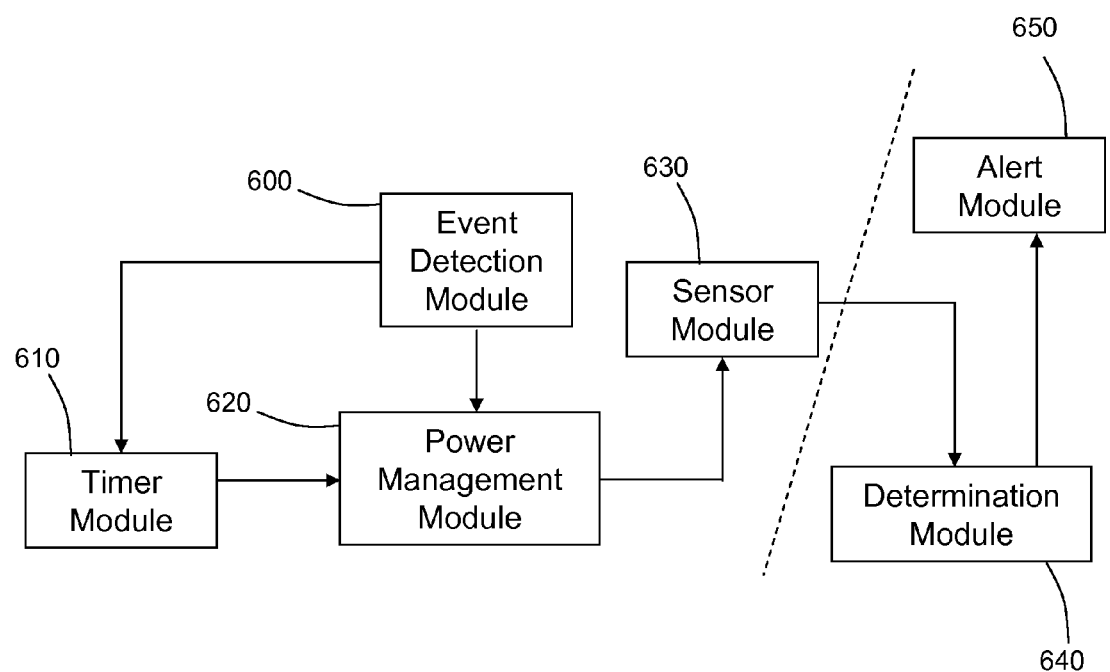

FIGS. 14A-C are block diagrams of representative devices or systems. It will be understood that one or more components described with regard to FIG. 6 may be included or carry out a function of one or more modules described in FIGS. 14A-C. As shown in FIGS. 14 A-C, a system or device suitable for carrying out one or more method as discussed with regard to FIGS. 7 and 9-13 may include an event detection module 600, a timer module 610, a power management module 620, a sensor module 630, a determination module 640, and an alert module 650. Event detection module 600 may detect an event (500) causing the activation of timer module 610 and power management module 620. Power management module 620 may activate sensor module (510) at appropriate time and deactivate sensor module (520) based on information from timer module (610). Determination module 640 may make a determination as to whether information from sensor module 630 is indicative of an infection (530). If the sensed information is indicative of infection, alert module 650 may provide an alert (540). As shown in FIG. 14A, all of the components may be included within an implantable medical device. Alternatively, some of the components may be included in an external device as shown in FIGS. 14B-C. The dashed lines in FIGS. 14B-C represent a distinction between implantable device and external device. Thus, as shown in FIG. 14B, alert module 650 may be included in an external device. In the embodiment shown in FIG. 14C, determination module 640 and alert module 650 may be included in an external device. Of course, a variety of other distributions of modules between an implantable medical device and an external device are possible.

One of skill in the art will understand that components or steps described herein regarding a given embodiment or set of embodiments may readily be omitted, substituted, or added from, with, or to components or steps of other embodiments or sets of embodiments, as appropriate or desirable.

It will be further understood that a computer readable medium containing instructions that when implemented cause an implantable medical device (or system including an implantable medical device) to perform the methods described herein are contemplated. In an embodiment the computer readable medium contains instructions that when implemented cause an implantable medical device to (i) detect a first event associated with the implanted medical device; (ii) activate a sensor module of the implanted medical device at or after the detection of the first event, the sensor module capable of detecting an indicator of infection; (ii) deactivate the sensor module two hours or more after the sensor module is activated; and (iii) determine whether information regarding the indicator of infection is indicative of an infection. Devices including the computer readable medium are also contemplated.

In addition, the principles of the methods, systems and devices described herein may be used for detecting various other potential adverse health issues associated with an implantable medical device. For example, temperature, pH, impedance, and various indicators of infection may also be used to determine whether a hematoma, edema, or seroma is present in proximity to an implanted device. Accordingly, monitoring of such other potential adverse health issues is within the scope of the present disclosure.

Patent applications directed to infection monitoring that may provide additional insight into the teachings provided herein include the following patent applications filed on even date herewith: (i) U.S. patent application Ser. No. 11/737,173, entitled "Infection Monitoring", naming Martin Gerber and John Rondoni as inventors; (ii) U.S. patent application Ser. No. 11/737,170, entitled "Infection Monitoring", naming Martin Gerber and John Rondoni as inventors; and (iii) U.S. patent application Ser. No. 11/737,179, entitled "Controlling Temperature During Recharge for Treatment of a Condition", naming Martin Gerber and John Rondoni as inventors. Each of the above-referenced patent applications are hereby incorporated herein by reference in their respective entireties to the extent that they do not conflict with the disclosure presented herein.

Thus, embodiments of EVENT-TRIGGERED INFECTION MONITORING are disclosed. One skilled in the art will appreciate that the present invention can be practiced with embodiments other than those disclosed. The disclosed embodiments are presented for purposes of illustration and not limitation, and the present invention is limited only by the claims that follow.

What is claimed is:

1. A method carried out by an implanted medical device or a system that includes the implanted medical device, comprising:
   detecting a first event associated with the implanted medical device;
   activating a sensor module of the implanted medical device at or after the detection of the first event, the sensor module capable of obtaining and transmitting information regarding an indicator of infection;
   deactivating the sensor module two hours or more after the sensor module is activated; and
   determining whether the information regarding the indicator of infection is indicative of an infection,
   wherein the implanted device is a refillable infusion device and wherein detecting the first event comprises detecting an event associated with refilling the device.

2. The method of claim 1, wherein detecting the first event comprises receiving instructions from a programmer that a refill event has commenced or is completed.

3. The method of claim 1, wherein activating the sensor module comprises providing power to a sensor from a power source of the implanted device.

4. The method of claim 1, wherein activating the sensor module comprises activating a circuit to store information provided by a sensor in memory of the implanted device.

5. The method of claim 1, wherein activating the sensor module comprises activating the module such that the module provides sensed information in discrete time intervals.

6. The method of claim 1, wherein deactivating the sensor module two hours or more after the sensor module is activated comprises deactivating the sensor module between two hours and 90 days after the sensor module is activated.

7. The method of claim 1, wherein determining whether information regarding the indicator of infection is indicative of an infection is determined in the implantable medical device.

8. The method of claim 1, further comprising sending the information regarding the indicator of infection to a second device, wherein determining whether information regarding the indicator of infection is indicative of an infection is determined in the second device.

9. The method of claim 1, further comprising:
   detecting a second even associated with the implanted medical device; and
   reactivating the sensor module at or after the detection of the second event.

10. The method of claim 9, wherein detecting the second event comprises detecting an event associated with a subsequent refilling the device.

11. The method of claim 10, wherein detecting the event associated with the subsequent refilling the device comprises receiving instructions from a programmer that the subsequent refill event has commenced or is completed.

12. The method of claim 9, further comprising deactivating the sensor module two or more hours after the reactivation of the sensor module.

13. The method of claim 1, wherein the sensor module is capable of obtaining and transmitting information regarding temperature.

14. The method of claim 1, wherein the sensor module is capable of obtaining and transmitting information regarding pH or impedance.

15. The method of claim 1, further comprising issuing an alert if the indicator of infection is indicative of an infection.

16. A non-transitory computer readable medium containing instructions that when implemented cause an implantable refillable infusion device to (i) detect an event associated with refilling the implanted medical device; (ii) activate a sensor module of the implanted medical device at or after the detection of the event, the sensor module capable of detecting an indicator of infection; (ii) deactivate the sensor module two hours or more after the sensor module is activated; and (iii) determine whether information regarding the indicator of infection is indicative of an infection.

17. An implantable refillable infusion device comprising the computer-readable media of claim 16.

18. The method of claim 1, wherein detecting the first event comprises detecting insertion of a needle into a refill port of the device.

19. The method of claim 9, wherein detecting the second event comprises detecting insertion of a needle into a refill port of the device.

* * * * *